United States Patent
Ko

(10) Patent No.: US 8,405,829 B2
(45) Date of Patent: Mar. 26, 2013

(54) PORTABLE ELECTRONIC DEVICE AND METHOD FOR TESTING POLARIZING ABILITY OF GLASS USING THE SAME

(75) Inventor: Chun-Cheng Ko, Taipei Hsien (TW)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 585 days.

(21) Appl. No.: 12/632,941

(22) Filed: Dec. 8, 2009

(65) Prior Publication Data

US 2011/0043494 A1 Feb. 24, 2011

(30) Foreign Application Priority Data

Aug. 18, 2009 (CN) .......................... 2009 1 0305755

(51) Int. Cl.
*G01J 4/00* (2006.01)
(52) U.S. Cl. ........................................ 356/364; 345/206
(58) Field of Classification Search ........................ None
See application file for complete search history.

(56) References Cited

U.S. PATENT DOCUMENTS

| 6,057,817 | A * | 5/2000 | Ono et al. | 345/94 |
| 6,618,027 | B2 * | 9/2003 | Takatori | 345/32 |
| 7,327,421 | B2 * | 2/2008 | Kaneko | 349/114 |
| 7,847,883 | B2 * | 12/2010 | Koma | 349/69 |
| 8,253,869 | B2 * | 8/2012 | Matsushima et al. | 349/12 |
| 2002/0071069 | A1 * | 6/2002 | Nakagawa et al. | 349/86 |
| 2003/0016188 | A1 * | 1/2003 | Takatori | 345/32 |
| 2003/0020672 | A1 * | 1/2003 | Takatori | 345/32 |

* cited by examiner

*Primary Examiner* — Jason Olson
(74) *Attorney, Agent, or Firm* — Altis Law Group, Inc.

(57) ABSTRACT

A portable electronic device includes a casing, a liquid crystal, a controlling module, and a button. The liquid crystal display is capable of emitting polarized light. The controlling module is received in the casing, the controlling module is configured for controlling the liquid crystal display to display a white screen when receiving a control signal. The button is configured for generating the control signal when triggered by a user.

6 Claims, 2 Drawing Sheets

PORTABLE ELECTRONIC DEVICE AND METHOD FOR TESTING POLARIZING ABILITY OF GLASS USING THE SAME

BACKGROUND

1. Technical Field

The present disclosure relates to portable electronic devices and, particularly, to a portable electronic device which can be used for testing polarizing ability of glasses.

2. Description of Related Art

At present, many types of sunglasses have been fabricated. Some of the sunglasses are made of polarizing glasses, and some of the sunglasses are made of semitransparent glass. However, both the polarizing glass and semitransparent glass can shield a portion of light emitted from a natural light source, such as sun etc, as a result, it is hard to distinguish whether the sunglass is made of polarizing glass or semitransparent glass by a common consumer.

What is needed, therefore, is a portable electronic device which can be used for testing polarizing ability of glasses to overcome the above-described problem.

BRIEF DESCRIPTION OF THE DRAWINGS

Many aspects of the present portable electronic device and method for testing polarizing ability of a glass can be better understood with reference to the accompanying drawings. The components in the drawings are not necessarily drawn to scale, the emphasis instead being placed upon clearly illustrating the principle of the present portable electronic device and method for testing polarizing ability of a glass using the same. In the drawings, all the views are schematic.

DETAILED DESCRIPTION

Embodiments of the present disclosure will now be described in detail below, with reference to the accompanying drawings.

Figure 1:
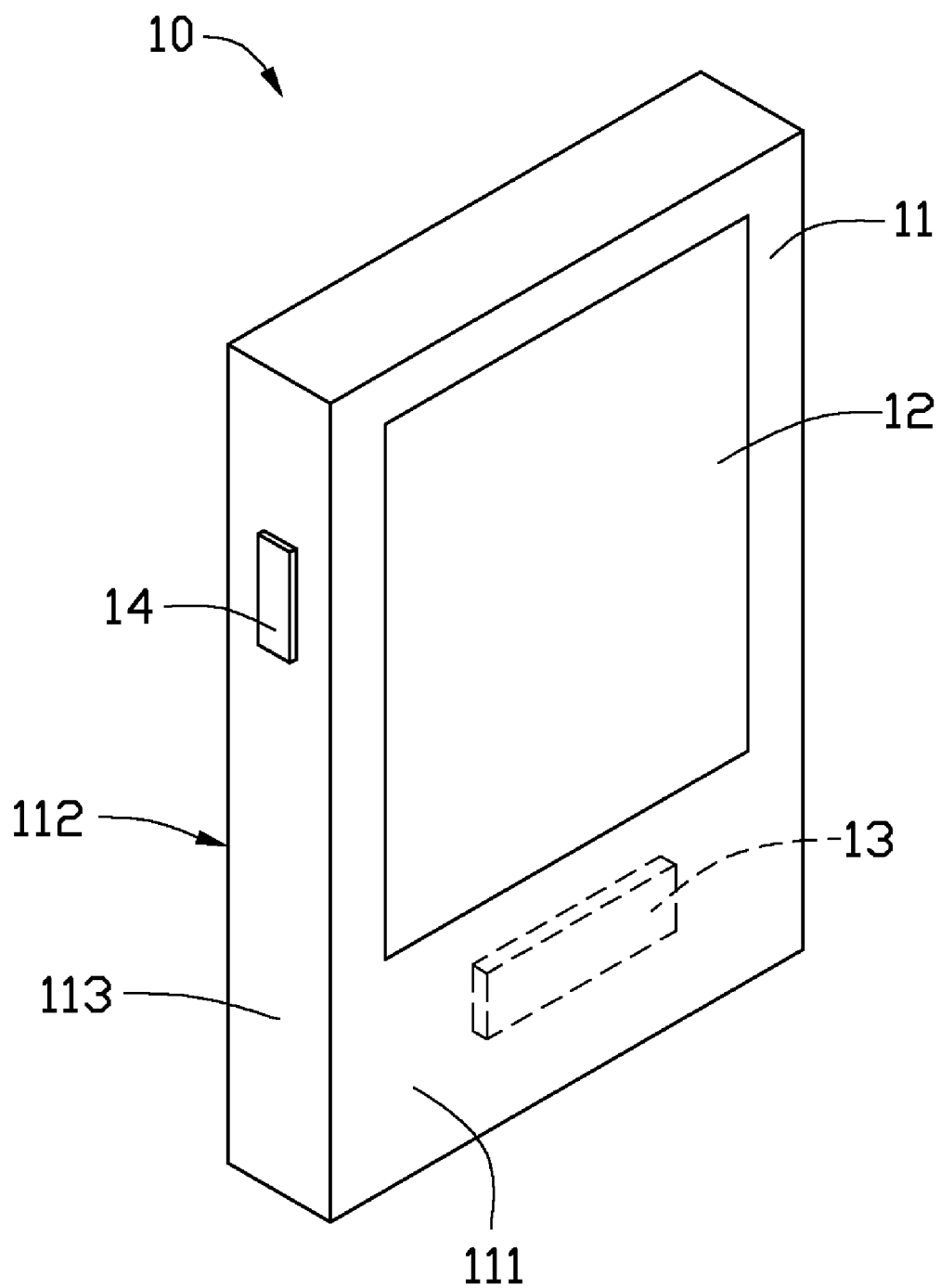
FIG. 1 is a schematic, isometric view of a portable electronic device according to an exemplary embodiment.

Referring to FIG. 1, a portable electronic device 10 according to an exemplary embodiment, is shown. The portable electronic device 10 includes a casing 11, a liquid crystal display 12, a controlling module 13, and a button 14. The portable electronic device 10 can be a mobile phone, a digital camera, an MP3, etc. In the present embodiment, the portable electronic device 10 is a mobile phone.

The casing 11 includes a front surface 111, a rear surface 112 opposite to the front surface 111, and a side surface 113. In the present embodiment, the casing 11 is substantially a cuboid, the front surface 111 is substantially parallel to the rear surface 112, and the side surface 113 connects the front surface 111 and the rear surface 112. The side surface 113 is substantially perpendicular to the front surface 111 and the rear surface 112.

The liquid crystal display 12 is disposed on the front surface 111 of the casing 11. The light emitted from the liquid crystal display 12 is polarized light. The liquid crystal display 12 is used for displaying data images.

The controlling module 13 is received in the casing 11. The controlling module 13 is electrically connected to the liquid crystal display 12, and can control the liquid crystal display 12 to display a white screen thereon when receive a control signal triggered by the button 14.

The button 14 can receive user's input and generate a control signal to control the controlling module 13. When users want to testing whether a glass is a polarizing glass, they can press the button 14 to generate a control signal, and the controlling module 13 will display a white screen on the liquid crystal display 12. Therefore, the portable electronic device can be used as a polarized light source for testing whether the glass is a polarizing polarized glass. In the present embodiment, the button is disposed on the side surface 113 of the casing 11.

Figure 2:
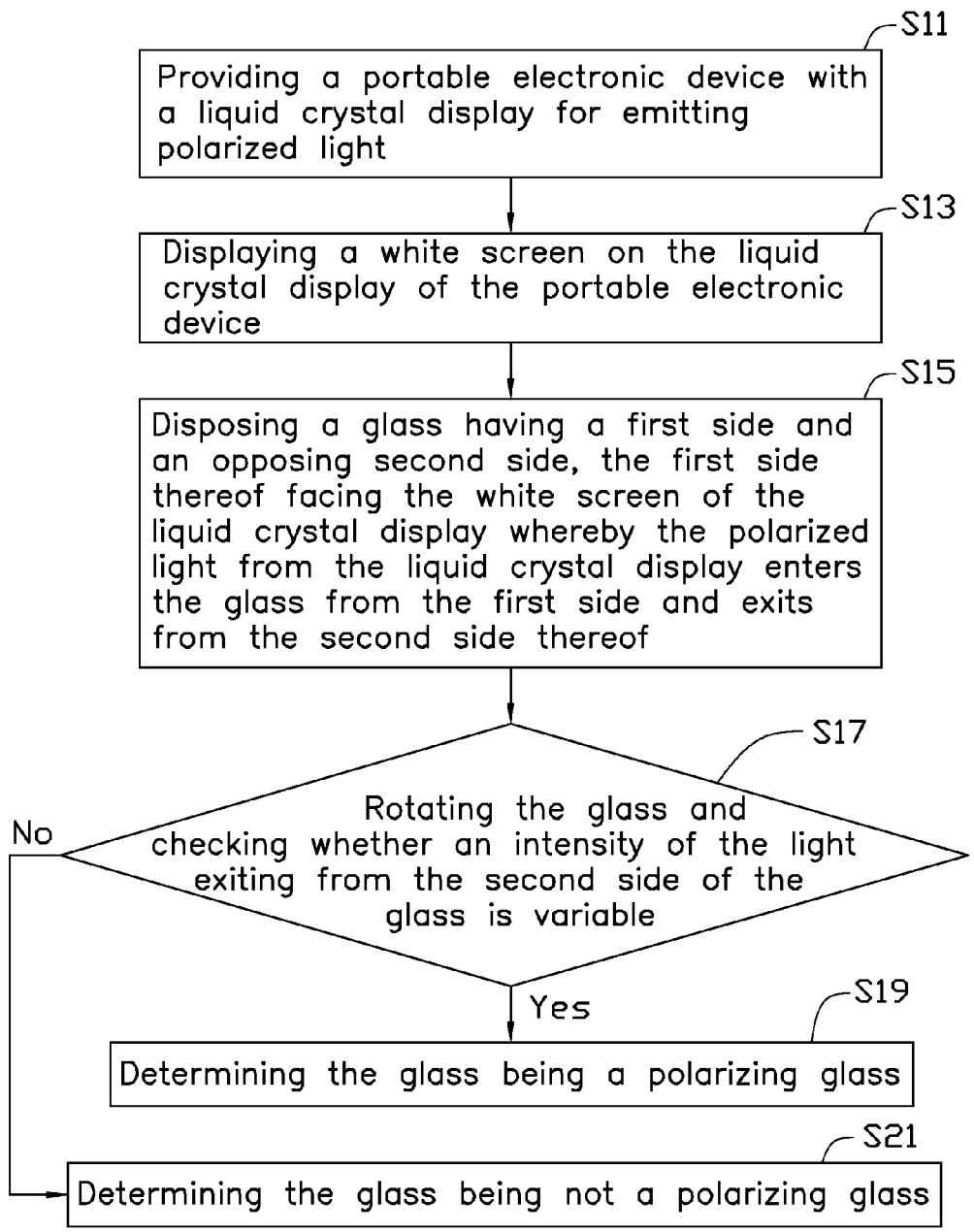
FIG. 2 is a flow chart of a method for testing polarizing ability of a glass according to an exemplary embodiment.

Referring to FIG. 2, a flow chart of a method for testing polarizing ability of a glass according to an exemplary embodiment, is shown. The method includes following steps.

Step S11: providing a portable electronic device 10 with a liquid crystal display 12 for emitting polarized light. In the present embodiment, the portable electronic device 10 is a mobile phone.

Step S13: displaying a white screen on the liquid crystal display 12 of the portable electronic device 10.

Step S15: disposing a glass having a first side and an opposing second side, the first side thereof facing the white screen of the liquid crystal display 12 whereby the polarized light from the liquid crystal display 12 enters the glass from the first side and exits from the second side thereof. The glass can be a polarizing glass, a semitransparent glass etc.

Step S17: rotating the glass and checking whether an intensity of the light exiting from the second side of the glass is variable.

Step S19: determining the glass being a polarizing glass if the intensity of the light exiting from the second side of the glass is variable while rotating the glass.

Step S21: determining the glass being not a polarizing glass if the intensity of the light exiting from the second side of the glass is variable is invariable while rotating the glass.

While certain embodiments have been described and exemplified above, various other embodiments will be apparent to those skilled in the art from the foregoing disclosure. The invention is not limited to the particular embodiments described and exemplified, and the embodiments are capable of considerable variation and modification without departure from the scope and spirit of the appended claims.

What is claimed is:

1. A method for testing polarizing ability of a glass comprising:
    providing a portable electronic device with a liquid crystal display for emitting polarized light;
    displaying a white screen on the liquid crystal display of the portable electronic device;
    disposing a glass having a first side and an opposing second side, the first side thereof facing the white screen of the liquid crystal display whereby the polarized light from the liquid crystal display enters the glass from the first side and exits from the second side thereof;
    rotating the glass and checking whether an intensity of the light exiting from the second side of the glass is variable;
    displaying the checking result of the light intensity to an operator.

2. The method of claim 1, wherein the portable electronic device is a mobile phone, a digital camera, or an MP3.

3. The method of claim 1, wherein the portable electronic device comprises a casing, the casing includes a front surface, a rear surface opposite to the front surface, and a side surface, the front surface is substantially parallel to the rear surface, and the side surface is substantially perpendicular to the front surface and the rear surface.

4. The method of claim 3, wherein the liquid crystal display is disposed on the front surface of the casing.

5. The method of claim 1, wherein the method further comprises determining the glass is a polarizing glass if the intensity of the light exiting from the second side of the glass is variable while rotating the glass.

6. The method of claim 1, wherein the method further comprises determining the glass is not a polarizing glass if the intensity of the light exiting from the second side of the glass is invariable while rotating the glass.

* * * * *